United States Patent [19]

McRae

[11] Patent Number: Plant 6,715

[45] Date of Patent: Apr. 4, 1989

[54] LILY PLANT NAMED 'DAWN PIXIE'

[75] Inventor: Edward A. McRae, Boring, Oreg.

[73] Assignee: Melridge, Inc., Aurora, Oreg.

[21] Appl. No.: 51,824

[22] Filed: May 18, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of hybrid lily plant bearing large clusters of flowers particularly characterized by their deep pink, gold centered coloration, the flowers being of excellent form and long persistence. The plant is of short stature having moderately long and full leaves and coupled with its medium sized, upright flowers, it is especially suitable as a pot plant variety. Also, its color pattern and silhouette are completely new in the upright Asiatic divisions of lilies suited to forcing and to mass commercial cultivation. The plant is highly resistant to disease and shows high tolerance of virus, making it an excellent garden plant, and its bulbs may be precooled and forced throughout the year for pot plant production.

1 Drawing Sheet

BACKGROUND OF THE INVENTION

This new variety of lily plant originated as a seedling selected from a group of seedlings planted by me at Sandy, Oreg., with the object of producing lilies in shades of pink and peach, well suited to forcing for pot plant production out-of-season, a product heretofore unknown in the lily breeding art.

The planting from which the present seedling was selected was made from seeds derived from a hybrid developed by my crossing the clonal cultivar 'Peachblush' (U.S. Plant Pat. No. 4,334) with a shorter pink seedling selected from the cross of 'Prince Charming'×'Harmony' (both unpantented) and my new seedling was selected for propagation and test because of its unusual flowers, which have a deep pink, gold throated coloration and copious elongated spotting, a color pattern unique in this type of lily plant. Asexual reproduction of this selected seedling was done by me and under my direction at Sandy, Oreg., with such pleasing results that, under my direction, successive generations produced by bulb scale propagation and by natural propagation from bulblets were grown and demonstrated that the novel and distinctive characteristics of my new variety would hold true from generation to generation under asexual propagation and appeared to be firmly fixed.

Work with this new plant has shown that the variety remains short and is not overly susceptible to bud abortion when forced into flower out-of-season as a pot plant; and in addition, the clone possesses to a high degree the desirable characteristics of hybrid vigor, great hardiness, and disease resistance; the new plant also possesses the characteristics of excellence of form, color and habit and the clone is a vigorous and good grower and propagator as observed at Sandy, Oreg. The new plant has been found to be well suited to forcing out-of-season when the bulbs are dug at the appropriate time and properly precooled. For example, October-dug bulbs, properly precooled and potted in January, will flower under glass in western Oregon in an average of sixty-five to eighty days with no supplementary lighting and at moderate greenhouse temperatures.

DESCRIPTION OF THE DRAWING

My new variety of lily plant is illustrated by the accompanying photographic drawing which, in full color, shows a three-fourths face view of a mature bloom and illustrates the flower form, tepal arrangement, and the novel and distinctive deep pink, gold centered flower coloration and its copious elongated spots, the colors depicted being as close to those herein specified as is reasonably possible to obtain by conventional photographic procedures.

DESCRIPTION OF THE NEW VARIETY

The following is a detailed description of my new variety of Asiatic hybrid lily, with nomenclature according to The International Lily Register by The Royal Horticultural Society of London, England, Second Edition, 1969; and with the color designations according to The R.H.S. Colour Chart published by the society in 1966.

THE PLANT

Origin: Seedling.

Parentage:

*Seed parent.*—Lilium 'Peachblush' (U.S. Plant Pat. No. 4,334).

*Pollen parent.*—A short, pink flowered hybrid Lilium seedling selected from the cross of 'Prince Charming'×'Harmony' (both unpatented).

Classification:

*Horticultural.*—Divison I-A, Upright Asiatic Hybrid Lily according to The Horticultural Classification of Lillies by The Royal Horticultural Society of London.

*Commercial.*—Hybrid Lilium Clone.

Form: A single stem, erect and stately.

Height: About 40 to 60 cm. for stems produced by glasshouse forcing of bulbs of about 12 to 18 cm. in circumference; provided that their light levels are adequate. Low light levels may cause "stretching".

Growth: Vigorous and upright.

Foliage:

*Quantity.*—Abundant.

*Leaf size.*—About 8 to 12 cm. long and about 5 to 12 mm. wide.

*Leaf shape.*—Linear with acuminate apex.

*Texture.*—Leathery.

*Appearance.*—Glossy and lightly pubescent.

*Color.*—Top side — Deep green. Under side — A lighter green.

Bulbs:

*Size.*—Varying, ranging to about 25 cm. in circumference as commercially used.

*Color.*—White.

THE BUD

Form: Long ovoid with obtuse apex and rounded base.

Size: About 8 to 9 cm. long and about 7 cm. in circumference just prior to opening.

Opening rate: The bud opens slowly, taking about one hour in response to morning light.

Color: Soft pink, 58D, with a flush of green along the midribs and at the tip prior to opening and as the tepals begin to unfurl.

Peduncle:

*Length.*—About 4 to 6 cm. in average; may lengthen somewhat if light levels are too low or if bulbs have been improperly stored prior to forcing.

*Color.*—Dark green.

THE FLOWER

Blooming habit: Annually, once and profusely in mid-season.

Size: Medium, averaging about 14 to 16 cm. in diameter.

Borne: In a single compact raceme having from 5 to 9 buds, from a bulb about 12 to 16 cm. in circumference.

Shape: Cup-shaped upon first opening and flattening as the tepals recurve during the second day.

Tepalage:

*Number.*—Six, hexagonally arranged and imbricated.

*Size.*—Outer tepals — Average about 2.5 cm. in width. Inner tepals — Average about 3 cm. in width.

*Color.*—Basic color — Red Purple, 59C, shading to 59D at the tepal margins and just parallel with the nectaries. A golden throat is formed by an area of Yellow-Orange, 23A-B, 1 to 2 cm. wide and extending along the center of each tepal for about 2 cm. outwardly from the nectary. The nectaries are cream to pink in color and are pubescent.

*Spotting.*—The tepals are conspicuously spotted with medium to large magenta colored spots which are elongated and occasionally merged and which extend lengthwise over the principal surface of each tepal for about two-thirds of the tepal length.

Pedicel:

*Length.*—About 4 to 8 cm., in average.

*Form.*—Sturdy and ascending upwardly to about 60 degrees from the horizontal.

*Color.*—Dark green and lightly pubescent.

Appearance: The flower is shiny.

Longevity: The tepals stay on the stems for about three weeks.

Color changes: The flowers may fade slightly to Greyed Purple, 186B-C, as the flower ages. Strong heat and light may reduce the pink pigmentation, but there is little change in the flower coloration if the light and temperature levels are suitable for cut flower and pot plant maintenance.

Fragrance: None.

Disease resistance: The flower and plant are resistant to disease; in particular, they are resistant to Fusarium bulb rot and Botrytis blight.

Lasting quality: The flower is long lasting, both on the plant and as a cut flower.

REPRODUCTIVE ORGANS

Stamens:

*Number.*—Six.

*Arrangement.*—Hexagonal, upper tepals slightly overlapping.

*Anthers (dehisced) and pollen.*—Color: Greyed Red, 178A.

*Filaments.*—Length: About 5 cm. Color: Soft pink, Greyed Purple 185B-C.

Pistils:

*Number.*—One.

*Length.*—About 5 cm.

*Stigma.*—Size: Medium to large. Color: Deep plum, Greyed Purple 185D.

Characteristics of ovary: The ovary is characteristic of the genus Lilium.

THE FRUIT

Fertility: The fruit is fertile.

Shape: Ovoid.

Color at maturity: Soft brown, sometimes overlaid with soft plum.

This new lily variety most closely resembles 'Pink Pixie' (Ser. No. 023,779) but it has a deeper pink coloration with a smaller gold colored throat rather than the cream throat of *Pink Pixie'. Also, the new plant has larger, widely spread, very conspicuous and elongated spots rather than the relatively inconspicuous, smaller spots located only at the center of the flower, as in 'Pink Pixie'.*

I claim:

1. The new and distinctive variety of Asiatic hybrid lily plant and parts thereof, substantially as herein shown and described, characterized by its conspicuously spotted and gold throated deep pink flowers; and by its short stemmed, abundantly leaved and upright flowering silhouette, ideal for pot plant culture.

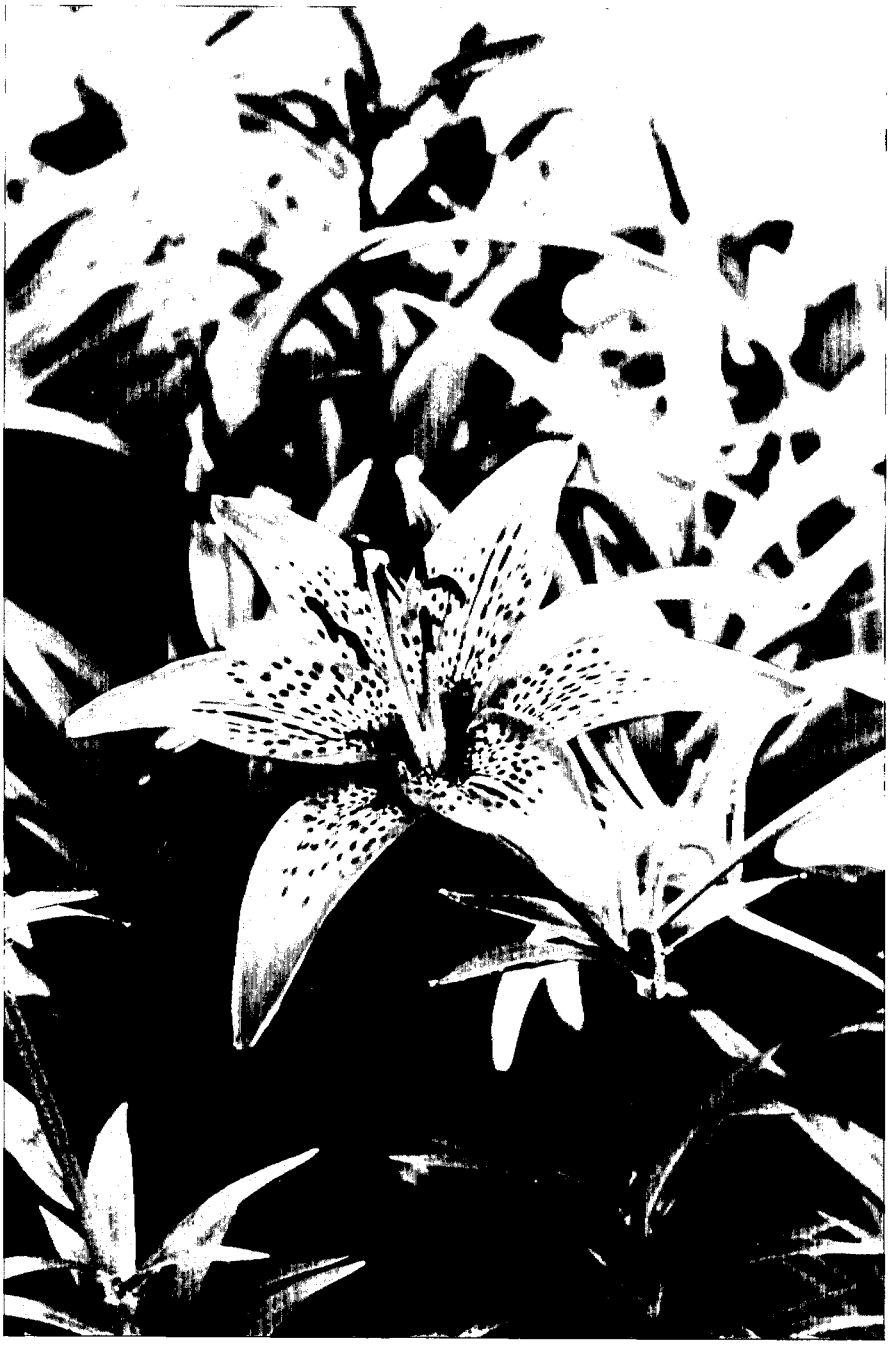

* * * * *